United States Patent [19]

Jurd

[11] 3,939,273
[45] Feb. 17, 1976

[54] 3,4-METHYLENEDIOXY-CINNAMYLOXYBENZENE AS A MOSQUITO LARVICIDE

[75] Inventor: Leonard Jurd, Berkeley, Calif.

[73] Assignee: The United States of America as represented by the Secretary of Agriculture, Washington, D.C.

[22] Filed: Mar. 5, 1975

[21] Appl. No.: 555,499

[52] U.S. Cl. ............................................. 424/282
[51] Int. Cl.² ......................................... A01N 9/28
[58] Field of Search .................................. 424/282

[56] References Cited

UNITED STATES PATENTS 3,796,726   3/1974   Edwards ..................... 424/282 X Primary Examiner—Jerome D. Goldberg
Assistant Examiner—Allen J. Robinson
Attorney, Agent, or Firm—M. Howard Silverstein; Max D. Hensley; William Takacs

[57] ABSTRACT

Method of destroying mosquito larvae by applying to them the compound 3,4-methylenedioxy-cinnamyloxybenzene.

2 Claims, No Drawings

3,4-METHYLENEDIOXY-CINNAMYLOXYBENZENE AS A MOSQUITO LARVICIDE

DESCRIPTION OF THE INVENTION

The invention relates to and has among its objects the provision of novel methods for destroying (killing) mosquito larvae. Further objects of the invention will be evident from the following description wherein parts and percentages are by weight unless otherwise specified. The abbreviation ppm used herein refers to parts per million. The symbol $\phi$ is used herein to represent the phenyl

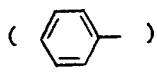

group.

One of the ways of controlling insect populations is to kill the insect larvae. Generally, a larvicide is applied to the breeding places or habitat of the insects where it destroys the larvae.

I have discovered that a certain organic compound is effective as a mosquito larvicide. When the compound of the invention is applied to the habitat of the mosquito, the larval population is substantially reduced.

The compound of the invention is 3,4-methylenedioxy-cinnamyloxybenzene. It has the structure

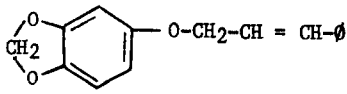

For the sake of brevity, this compound is hereinafter referred to as MDCB.

As disclosed in my copending application Ser. No. 555,488 filed Mar. 5, 1975, the disclosure of which is incorporated herein by reference, MDCB may be prepared by reacting sesamol (also known as 3,4-methylenedioxy-phenol) with cinnamyl chloride in the presence of a base such as potassium carbonate to convert the hydroxy group of sesamol to a cinnamyloxy group ($-O-CH_2-CH=CH-\phi$).

MDCB is highly effective in killing mosquito larvae. Generally, for such purpose MDCB is applied to the breeding place of the mosquito—such as a body of water—in a concentration of about 1 to 10 ppm. Because MDCB is effective in very minor concentration, it is preferred that it be dissolved or suspended in an appropriate carrier prior to application to the breeding center. The solution or suspension increases the bulk and thus allows small amounts of MDCB to be administered to the mosquito's habitat. For such purpose it is preferred to use highly-volatile solvents such as acetone, ethyl ether, ethanol, benzene, xylene, or the like.

EXAMPLES

The invention is further demonstrated by the following illustrative examples.

Example 1 — Preparation of 3,4-Methylenedioxy-Cinnamyloxybenzene (MDCB)

A mixture of sesamol (27.6 g.), cinnamyl chloride (30.4 g.), anhydrous potassium carbonate (50.0 g.), potassium iodide (2.0 g.) in anhydrous acetone (100 ml.) was heated under reflux for 1.5 hrs. The acetone was removed by evaporation, and the residue was treated with excess water and cooled to give an oil, which subsequently solidified. The crude product was collected by filtration and recrystallized from methanol to give MDCB as colorless prisms, m.p. 83° C., yield 15.0 g. (Found: C, 75.4; H, 5.67. Calculated for $C_{16}H_{14}O_3$: C, 75.6; H, 5.55.) The nuclear magnetic resonance (NMR) spectrum of MDCB at 100 MHz in deuterated chloroform ($CDCl_3$) exhibited absorbances as follows: a doublet (2 protons) at $\delta$ 4.59 (coupling constant J = 6.0 Hz), singlet (2 protons at $\delta$ 5.89, a multiplet (5 protons) at $\delta$ 6.22–6.80, and a multiplet (5 protons) at $\delta$ 7.18–8.48.

Example 2 — Mosquito Larva Tests

Early fourth-instar larvae of *Anopheles quadrimaculatus Say* were exposed to a suspension of MDCB in water (duplicate tests). The suspension was prepared by adding a solution of MDCB in acetone to the water and evaporating the acetone. Mosquito larvae were added to the treated water and mortality was determined after 24 hrs. of exposure. The results are summarized as follows:

| Compound | Concentration, ppm. | Mortality after 24 hrs., % |
|---|---|---|
| MDCB | 10 | 76 |
| do. | 1 | 70 |

Having thus described the invention, what is claimed is

1. A method for killing mosquito larvae which consists of applying to a body of water where the larvae are located a larvicidal amount of 3,4-methylenedioxy-cinnamyloxybenzene.

2. The method of claim 1 wherein the stated compound is applied in a concentration of about 1 to 10 ppm.

* * * * *